United States Patent [19]

Plys et al.

[11] 4,427,305
[45] Jan. 24, 1984

[54] ANALYZER FOR DISTILLABLE MATERIALS

[75] Inventors: Albert G. Plys, South Holland, Ill.; Thorpe Dresser, Green Valley, Ariz.; Stanley Ohlswager, Olympia Fields; Lee G. Peterman, Flossmoor, both of Ill.

[73] Assignee: Atlantic Richfield Company, Philadelphia, Pa.

[21] Appl. No.: 282,462

[22] Filed: Jul. 13, 1981

[51] Int. Cl.³ .................................................. G01N 25/14
[52] U.S. Cl. ...................................... 374/45; 73/61.1 R
[58] Field of Search ..................... 73/25, 61.1 R, 61.3; 374/45, 112; 208/347

[56] References Cited

U.S. PATENT DOCUMENTS

| | | | |
|---|---|---|---|
| 3,264,862 | 8/1966 | Felton et al. | 73/25 |
| 3,354,052 | 11/1967 | Williams | 73/25 |
| 3,521,479 | 7/1970 | Carter | 73/25 X |
| 3,535,915 | 10/1970 | Felton et al. | 73/25 |

*Primary Examiner*—Herbert Goldstein

[57] ABSTRACT

Disclosed is an analyzer for determining volatile composition changes of a distillable material which comprises: (a) a first device for causing at least a portion of said material to be at a temperature and at a pressure so that a difference in temperature of said portion of said material across an isenthalpic expansion at critical flow conditions would be at least about 5° F.; (b) a second device for carrying out said isenthalpic expansion on said at least a portion of said material; (c) a third device for measuring at least two temperatures of said material where said at least two temperatures are a first and a second temperature, said first temperature being measured upstream of said expansion and said second temperature being measured downstream from said expansion; and (d) a fourth device for maintaining pressure downstream of said expansion to a value which does not vary by an amount in excess of about 20% of said pressure downstream of said expansion. The disclosed analyzer can be used in conjunction with equipment useful for processing distillable material into various boiling fractions. Disclosed also is a particular application for the analyzer in an online configuration for refining of petroleum crudes.

17 Claims, 4 Drawing Figures

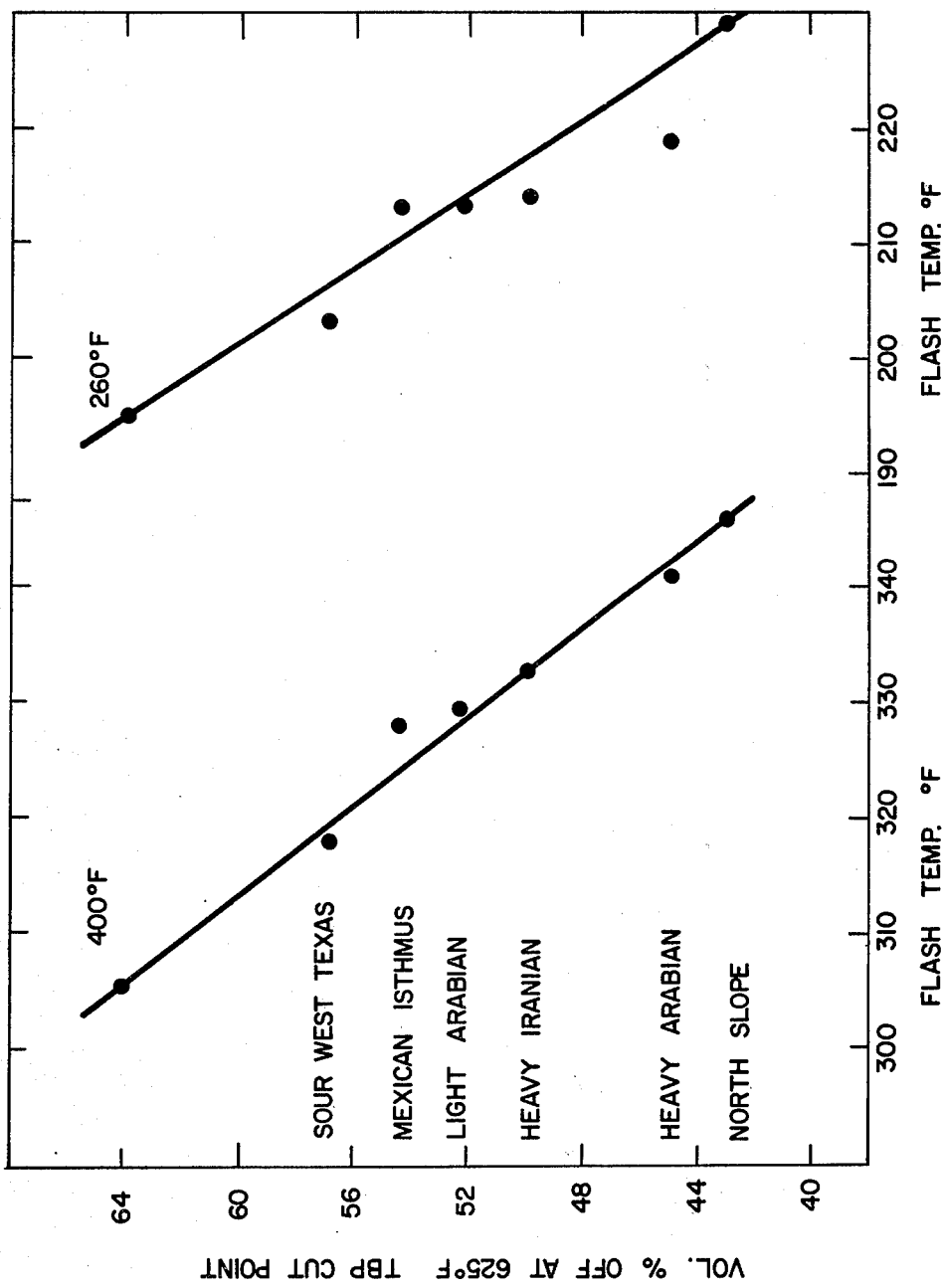

ANALYZER FOR DISTILLABLE MATERIALS

BACKGROUND OF THE INVENTION

This invention relates generally to analytic devices for distillable materials. More particularly, this invention relates to on-line petroleum crude analyzers which provides relevant information useful in controlling process variables so as to optimize distillation efficiencies and other interconnected downstream processes in a refinery.

Methods for analyzing petroleum crude feed stocks which involve complex analytical procedures are well known in the petroleum industry. For example, gas-liquid chromatograms utilizing spectrophotometric techniques can achieve a significant compositional breakdown of a petroleum crude sample. Such complete description of the crude sample can then be used to precisely define and optimize process variables to maximize both yields and general operating efficiency of a refinery.

Another method for analyzing a petroleum crude involves classification and hydrocarbon type analysis. In this method, the crude is distilled at atmospheric pressure into fractions having a boiling point up to 275° C. and then further distilling at 40 mm of Hg into fractions boiling above 275° C. Subsequently, specific gravities of each fraction are determined and the crude classified accordingly.

Unfortunately with the wealth of information available from analyzing crudes, at least two problems have persisted. The first is the complexity of equipment necessary to obtain required information. The second is the inability to obtain rapidly enough the required information to take into account sudden and often unexpected changes in the crude or hydrocarbon feedstock so as to vary appropriately process control elements such as valves and heaters.

BRIEF DESCRIPTION OF THE INVENTION

It is an object of this invention to provide a simple on-line system for detecting changes in distillable materials such as petroleum crudes which avoids the problems associated with complex analytical systems currently available.

It is an object of this invention to provide a system, which is both simple to operate and maintain, e.g., no moving parts, and has on-line operational reliability, responsive to moment-to-moment changes in a distillable material.

It is an object of this invention to provide a device which produces a temperature difference across an expansion of a distillable material wherein the amount of components in that material which are volatile at some temperature and pressure of interest is correlatable to that temperature difference.

Other objects of this invention are clear based upon this specification.

Briefly, this invention involves an isenthalpic expansion or flash of a portion of a distillable material, e.g., petroleum crude stream. More specifically the expansion is conducted so as to produce a differential temperature across the expansion of at least about 5° F. (2.8° C.) as discussed in more detail in EXAMPLE 5. The flow rate preferably is determined by two-phase critical flow. During two-phase flow at critical conditions, the rate of flow of a fluid is pressure dependent only on upstream pressure and is independent of pressure which is downstream of the expansion. Flow rates in the range of about 20 to about 600 pounds per hour and preferably about 50 to about 500 pounds per hour have been found useful.

For the system of this invention to work the impact of several process variables on flow rate must be small. Process variables which can impact the on-line functioning of this invention include: petroleum crude type, supply temperature fluctuations, supply pressure fluctuations, vacuum column pressure fluctuations and various combinations thereof.

It has been found that the critical process variables that are involved in an on-line configuration as shown in FIG. 1 are so small as to not adversely impact operation of an apparatus of this invention. This is especially true with respect to the flow rate of a material through an analyzer or device of this invention.

It has been discovered that an analyzer of this invention can control the flow rate of material to a value that does not vary by more than about 20%, and preferably to a value that does not vary by more than about 10% by means of an expansion at critical flow conditions so as to not require any moving parts.

As shown in the examples fluctuations in supply temperature and pressure, and vacuum column pressure do not dramatically affect (1) the observed difference in temperature across an isenthalpic expansion, Delta T ("$D_T$") or (2) the critical flow rate through the on-line crude analyzer of this invention, provided undue thermal losses are avoided.

A petroleum crude thoughout this Specification and claims shall mean a naturally occurring mixture, consisting predominately of hydrocarbons and/or of sulfur, nitrogen and/or oxygen derivatives of hydrocarbons, which is removed from the earth in liquid state or is capable of being removed. Petroleum crude is commonly accompanied by varying quantities of extraneous substances such as water, inorganic matter, and gases. The removal of such extraneous substances alone does not change the status of the mixture as a petroleum crude, unless such removal appreciably affects the composition of the mixture.

A hydrocarbon feedstock as used throughout this Specification is intended to include petroleum crudes and petroleum crudes which have been processed to some degree. Since one of the important purposes of this invention is to provide information useful for deciding how to modify process controls so as to take into account variations in a stream to a distillation column, any stream which varies or is likely to vary and which is a feed stream to a distillation column is contemplated by this invention.

Broadly, this invention comprises an analyzer for determining changes in a distillable material of the amount of components which are volatile at a particular temperature and pressure. Significant changes in the amount of volatile components can adversely impact the efficiency of a distillation column such as a petroleum crude still in a refinery. For example, if there is a significant change in the amount of lower boiling components present in a distillable material then the distillation column receiving such material could be adversely impacted due to improper heating of the material prior to its entering the still. Knowing that there is a significant change in the amount of volatile components present, an operator could and probably would change the amount of heat introduced into such a material prior to its entering the distillation column. Other process controls which an operator could and probably would change are valves. The takeoff valves for different components, e.g., different boiling point range fractions, would be varied so as to permit more volatiles to be removed so as to maintain the proper vapor-liquid equilibrium balance throughout the distillation column.

Broadly, an analyzer of this invention for determining composition changes of a material comprises several interacting parts. These individual parts will now be discussed in more detail hereinafter.

One of these parts is a means for causing a distillable material to be at such a temperature and pressure that a temperature difference in the material across an expansion of the material at isenthalpic flash conditions will be at least about 5° F. (2.8° C.).

A second part comprises a second means for expanding the material at isenthalpic flash conditions in an expansion at critical flow conditions so as to cause a differential temperature in the material across that expansion of at least 5° F. (2.8° C.). The expansion is preferably a free expansion so as not to involve any work being done by or on the material. A system undergoes an isenthalpic process, e.g., expansion, when two conditions are met: (1) no work is done on or by the system during the process and (2) the process is carried out adiabatically.

Another part of this invention involves a means for measuring at least two temperatures of the material. The first temperature is upstream of the above described isenthalpic expansion, and the second temperature is downstream from the isenthalpic expansion. Preferably, the upstream temperature is measured immediately preceding the expansion and the downstream temperature is measured immediately following the expansion so as to avoid any variation in observed temperature upstream or downstream of the expansion which might result from heat transferred to or from the system.

Finally, there is a fourth part which is a means for maintaining pressure downstream of the expansion. It is preferable to maintain pressure downstream of the expansion to a value which does not vary to any substantial amount. A substantial amount is any amount which impacts to any substantial degree observed temperature differences. As discussed in the EXAMPLES, a variation in downstream pressure will have an impact on the observed temperature difference across an isenthalpic flash or expansion. This observed temperature difference across the expansion will vary if the downstream pressure is varied significantly, because the amount of volatiles during such an expansion that go from a liquid to a vapor state vary depending upon downstream pressure. It has been found that a value in pressure variation which does not cause a significant change in observed difference in temperature acrosss an expansion of a petroleum crude is one which is less than about 20% of the flash zone pressure and, preferably, less than about 10% of the flash zone pressure. In an EXAMPLE, it was found that a variation in downstream pressure of flash zone pressure of no more than 20 millimeters of mercury did not give rise to an observed range in temperature for a particular material of more than 2° or 3° F. Downstream pressures after the expansion in the range of about 30 mm of Hg to about 250 mm of Hg, and preferably about 50 mm of Hg to about 150 mm of Hg have been found to be useful in this invention for petroleum crudes.

A greater change than 5° F. (2.8° C.) in observed temperature difference across an expansion will provide greater accuracy as to compositional changes in the material. However, larger temperature changes usually occur only when the material has been heated to higher temperatures and pressures prior to the expansion. At higher temperatures and pressures, there is greater likelihood of some decomposition of the material being expanded. Extensive or significant decomposition, of the material is, of course, to be avoided since it results in deposits and undesirable side reactions. Generally, petroleum crudes do not undergo substantial thermal decomposition below about 650° F. (353° C.). Temperatures in the range of about 200° F. (93° C.) to about 650° F. (353° C.), preferably, about 300° F. (150° C.) to about 500° F. (260° C.) and pressures in the range of about 5 pounds per square inch absolute (psia) to about 165 psia have been found useful in this invention just upstream of an isenthalpic expansion for petroleum crudes.

In still another embodiment of this invention, there is involved the combination of the analyzer described above in an on-line configuration with any apparatus useful for distillation.

It has been found that a vacuum still conventionally used in refineries can be of such a size and nature that a change in pressure of a vacuum still can be maintained in the range of less than about 50 mm of mercury and more preferably, to less than about 20 mm of mercury.

In still another embodiment, this invention involves a process for carrying out an isenthalpic expansion in such a manner that there is a temperature difference in the material across the isenthalpic expansion of at least about 5° F. (2.8° C.). An isenthalpic process of a system involves any process which is both (1) adiabatic, and (2) carried out in such a way that no work is done either on or by the system.

In still a more particular form, the process of this invention involves determining a volatile composition of a distillable material while that material is being transferred to a distillation column. Firstly, at least a portion of the material being so transported is diverted to form a first stream. Secondly, at least a portion of this first stream is caused to be at a temperature and a pressure so as to form a second stream. The temperature and pressure are so selected so that an isenthalpic expansion at critical flow conditions of the second stream will result in a temperature difference in that second stream across that expansion to be at least about 5° F. (2.8° C.) and still more preferably at least about 10° F. (5.6° C.). Thirdly, the second stream is expanded at isenthalpic conditions and critical flow conditions so as to produce a temperature change across the isenthalpic expansion at critical flow conditions of at least about 5° F. at more preferably at least about 10° F. while maintaining pressure downstream of the isenthalpic expansion to a value that does not vary by an amount in excess of about 20% of that value and still more preferably 10% of that value. The temperature change across the expansion in the second stream is a useful measure of volatile composition of the second stream.

The temperature and pressure desirable for the distillable material just prior to the isenthalpic expansion is not critical except to the extent that it does provide the required at least 5° F. (2.8° C.) temperature change across the expansion. Clearly, a greater temperature change across the expansion would be more desirable because it does permit a more accurate determination of the volatile composition. However, higher temperature and pressures will lead to the possibility of greater decomposition and other side reactions which are undesirable.

A distillable material as used throughout this specification and claims is intended to cover any material which is at least partially distillable.

An isenthalpic process as used throughout this specification and claims is intended to include a substantially isenthalpic process. The purpose of using an isenthalpic process is to minimize to as great an extent as reasonable energy transfer to and/or from a system during an expansion of that system. If an observed temperature difference across an expansion can be correlated to the amount of volatile components present in a distillable material, then the purpose for carrying out the expansion has been achieved. A linear correlation between a temperature difference across an isenthalpic flash of a series of different petroleum crudes and the respective percent by volume amount of components volatile at about 625° F. (330° C.) and one atmospheric pressure is shown in FIG. 4.

BRIEF DESCRIPTION OF THE FIGURES

FIG. 4 shows the relationship between different crude feeds and the temperature of isenthapic flashing of such crude feeds.

DETAILED DESCRIPTION OF THE INVENTION

Figure 1:
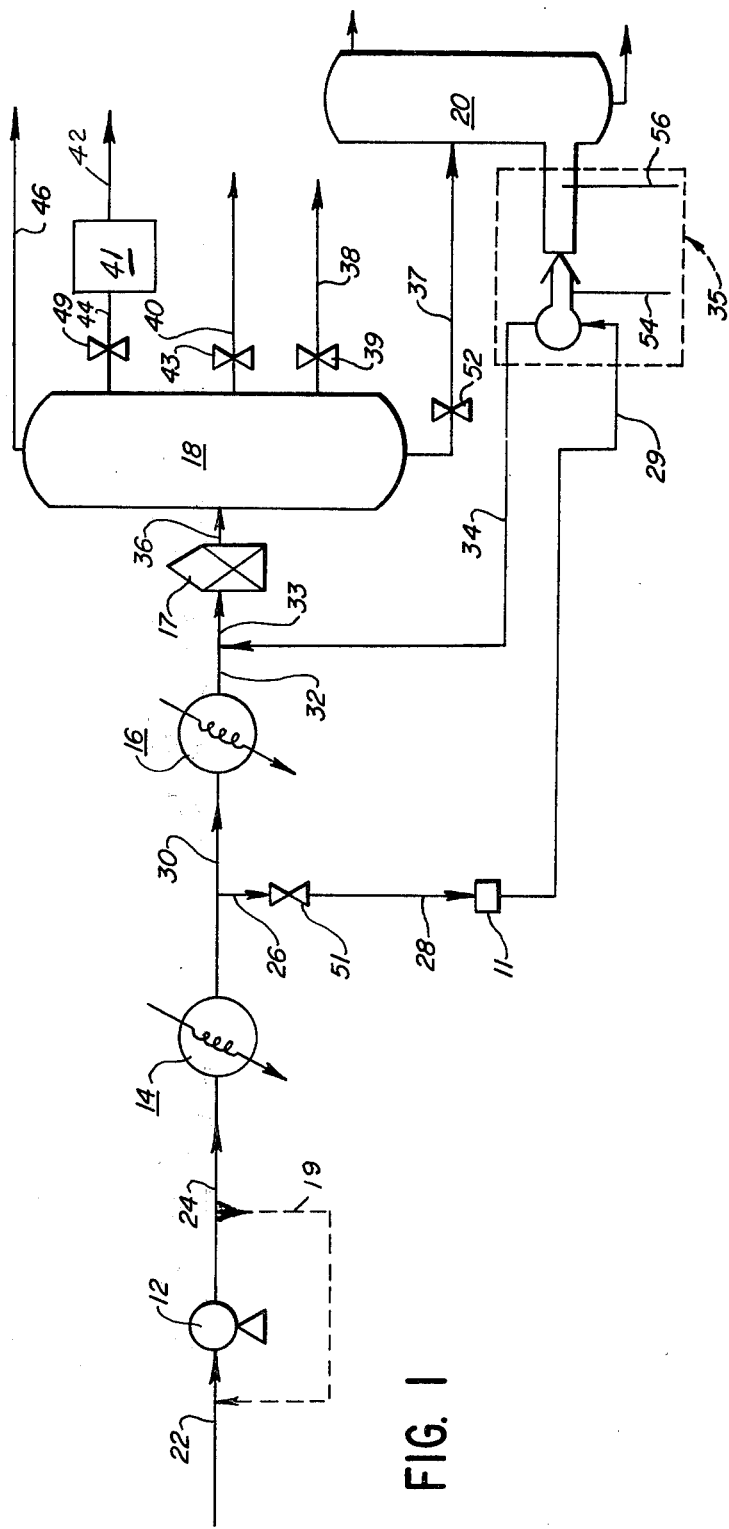
FIG. 1 discloses a crude line to a crude still and the various streams away from a typical refinery crude still, wherein crude analyzer of this invention is tied into the crude line leading to the still.

FIG. 1 discloses pumps 11 and 12 heat exchangers 14 and 16, a heater 17, a crude still or distillation column 18, a vacuum still 20, an on-line crude analyzer of this invention 35, valves 39, 43, 49, 51 and 52 conduits 22, 24, 26, 28, 29, 30, 32, 33, 34, 36, 37, 38, 40, 42, 44 and 46 and a catalytic reforming zone 41.

Crude oil or petroleum crude is transferred by conduit 22 under the influence of pump 12 through conduit 24 and into heat exchanger 14. The crude carried by conduit 24 is raised to a temperature of at least about 350° F. at a pressure of about 450 psig. Part of the crude exiting heat exchanger 14 is carried by conduit 26 through valve 51 and into conduit 28. Conduits 26, 28, 29 and 34 provide a loop for a portion of the crude exiting from heat exchanger 14. Alternatively, this loop including conduits 26, 28, 29, and 34 shown in solid lines coming from conduit 30 and re-entering the crude line into conduit 32, can instead be located as shown schematically by dotted lines 19 from conduit 24 and re-entering into conduit 22. The alternative location for the loop was discovered feasible because of the rapid heat equilibration shown to be possible in EXAMPLE 5. Also, the alternative location can eliminate the need for an additional pump such as pump 11 within the loop shown in FIG. 1. The details involving the crude in this loop will be discussed with respect to FIG. 2.

Crude not transferred through valve 51 is transferred in conduit 30 to a second heat exchanger 16. The material then exits through conduit 32 and enters conduit 33. Conduit 33 carries the material into heater 17 and then through conduit 36 into crude still 18.

The material entering distillation column or crude still 18 from conduit 36 is fractionated into several streams which exit through conduits 37, 38, 40, 44, and 46. One stream exiting still 18 through valve 52 and conduit 37 is the resid stream consisting of heavy crude which have a boiling point of about 650° F. (343° C.) and which is further fractionated in a vacuum still 20. The temperature of the resid stream exiting conduit 37 is at a temperature of about 650° F. (343° C.) to about 700° F. (370° C.) and a pressure of about 5 psig to about 50 psig. A second stream exiting through valve 39 and conduit 38 is a diesel stream, which has a boiling point range of about 525° F. (274° C.) to about 650° F. (343° C.). This diesel stream can optionally be used as a heat transfer medium for heat exchangers 14 and/or 16. A third stream exiting still 18 through valve 43 and conduit 40 consists of hydrocarbons having a boiling point range of from about 380° F. (193° C.) to about 525° F. (274° C.). A fourth stream exiting still 18 through valve 49 and conduit 44 consists of hydrocarbons having a boiling point range of from about 200° F. (93° C.) to about 380° F. (193° C.). The stream carried in conduit 44 contains $C_5$ and above hydrocarbons especially suited to reforming. Box 41 is a schematic representation of one or more catalytic reforming zones. Conduit 42 removes any reformed product to appropriate processing and/or storage zones as required and well understood in the art. Finally, exiting still 18 in conduit 46 are light hydrocarbons ($C_1$ to $C_4$'s) and hydrogen.

Figure 3:
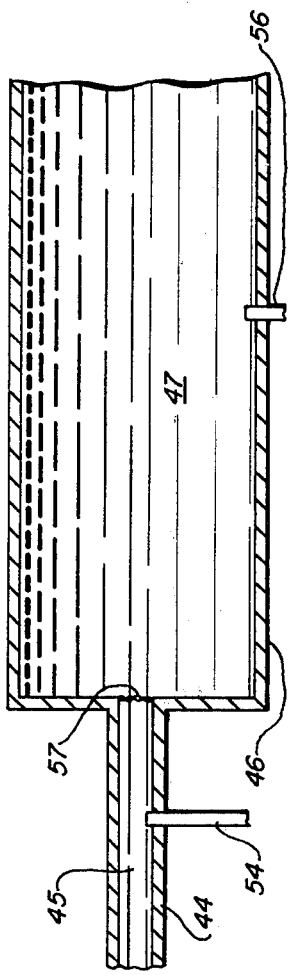
FIG. 3 is an enlarged view of an expansion chamber useful for on-line analysis of a crude feed.
Figure 2:
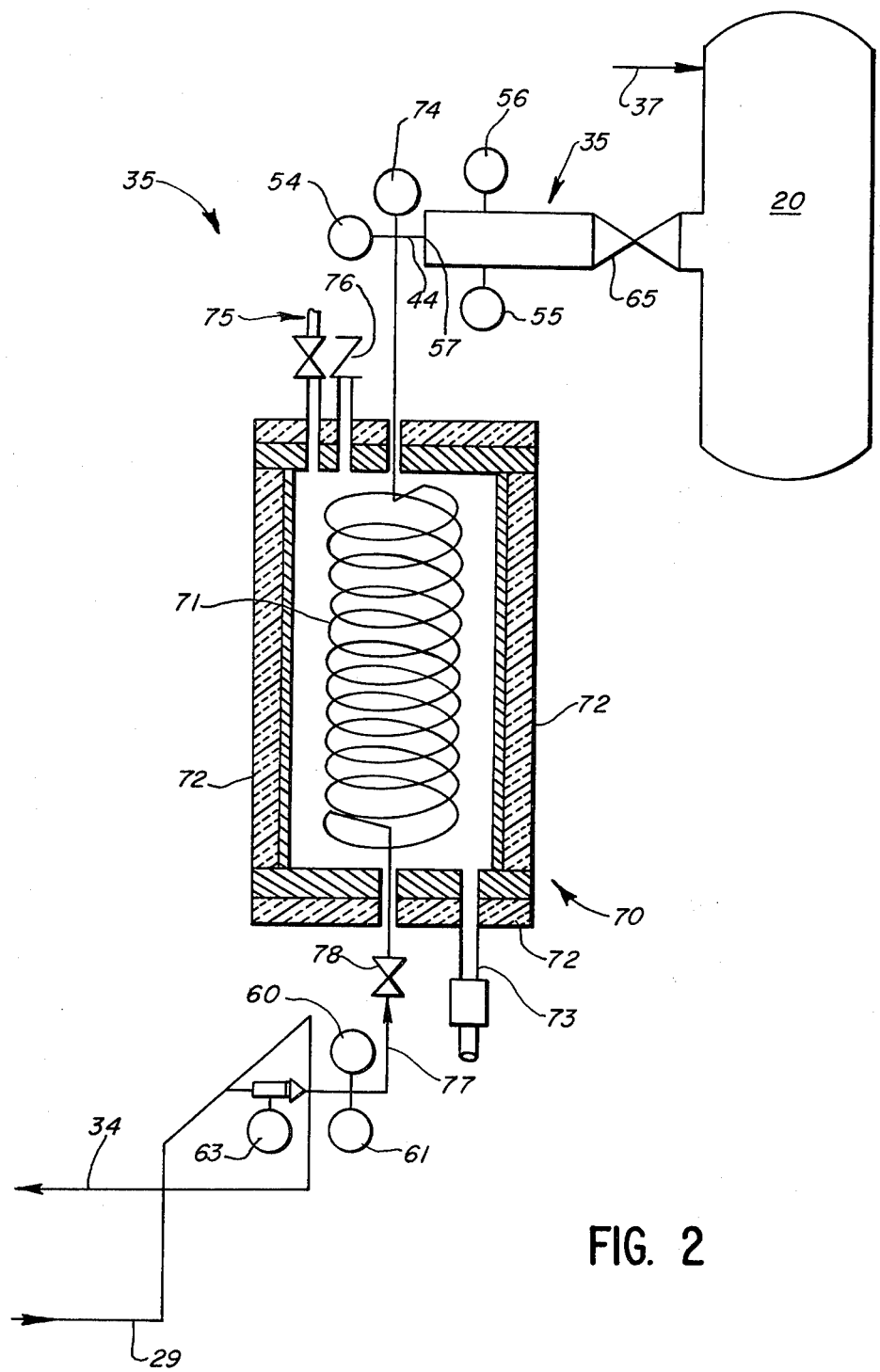
FIG. 2 is an enlarged detailed view of the apparatus disclosed in dotted area 35 of FIG. 1.

FIG. 2 discloses a device used to test the feasibility of using a critical flow isenthalpic two-phase free expansion as a method for indicating changes in crude feedstocks based upon observed changes in temperature measured at temperature indicators 54 and 56 shown in more detail in FIG. 3.

FIG. 2 discloses a device comprising the following elements: conduits 29 and 34, flow measuring indicator 63, supply pressure indicator 61, supply temperature indicator 60, steam trap 70, coil 71, insulation 72, condensed water outlet 73, connection 75 for 125 lbs or psig steam, a pressure relief valve 76, a temperature indicator 54, a pressure indicator 74, a temperature indicator 56, a pressure indicator 55, a block valve 65 and a vacuum still 20.

Coil 71 comprises ¼" stainless steel tubing wrapped to an inside diameter coil of 4" having a length of approximately 142 feet. Steam trap 70 has insulation 72 to maintain temperature of the 125 lbs steam which enters through connection 75 and exits through condensed water outlet 73. The precise dimensions of coil 71, expansion zone 47 and steam trap 70 are not critical, except that the distillable material, e.g., petroleum crude being transferred therethrough has a temperature and a pressure just upstream of an isenthalpic flash at critical flow conditions so that two conditions are fulfilled: (1) a temperature difference across the expansion is at least 5° F. (2.8° C.) and preferably at least 10° F. (5.6° C.) and (2) the critical flow rate through expansion zone 47 is not in excess of about 600 pounds per hour. A useful working range for critical flow in this invention has been found to be about 20 to about 600, and preferably, about 50 to about 500 pounds per hour. Too much flow results in a loss in distillation efficiency as well as an overwhelming of vacuum still 20 steam jets. Too little flow will make it difficult to obtain a desirable response time for analyzing a material, and also implicit in lower flow rates are smaller diametered conduits. With smaller conduits, there is a greater likelihood of plugging.

The tests used to confirm the feasibility of using an isenthalpic free expansion at critical flow conditions involved primarily an apparatus 35 of FIGS. 2 and 3. A portion of crude carried from an exchanger train consisting of conduits 22, 24, 30, and 32 which include heat exchangers 14 and 16 is carried by conduit 29 and through a flow indicating device 63 into conduit 77 passed a valve 78 and then through coil 71 into conduit 44 which leads to orifice 57 and expansion space 47. The expansion chamber is shown in enlarged scale in FIG. 3. The portion of the crude not entering conduit 77 is returned through conduit 34 shown in FIG. 1. The amount of material flowing through conduits 29 and 34 are about 9 and about 10 barrels per hour, respectively. Only a fraction of about 10% by total weight of the material carried in conduit 29 enters the device shown in FIGS. 2 and 3. A barrel here means 42 U.S. gallons measured at 60° F. (15.5° C.) at one atmosphere of pressure.

EXAMPLE 1

One variable likely to affect flow rates through a crude analyzer of this invention involves changes in crude source, e.g., changes from a heavy crude such as North Slope crude to a light crude such as a Nigerian Light crude. Table 1 summarizes calculated flow rates for North Slope and Nigerian Light crudes and water.

TABLE 1

EFFECT OF CRUDE CHANGES ON CRITICAL FLOW THROUGH COMMERCIAL APPARATUS
Equivalent Length = 190 ft.
Inside d = 0.120 in.
of Coil 71

| Crude Type | Supply | | Pressure Upstream of Expansion | |
|---|---|---|---|---|
| | Pressure psig | Temp. °F. | $P_u$ psia | Flow #/hr |
| North Slope | 400 | 353 | 45 | 305 |
| Nigerian Light | 400 | 353 | 59 | 310 |
| Water | 400 | 353 | 122 | 335 |

Flow rate did not vary by more than two percent (2%) between the two different types of crudes through the free expansion under critical flow conditions. The initial supply temperatures and pressures were 353° F. and 400 psig, respectively. The supply pressure of 400 psig was reduced during passage through coil 71 to a value just upstream of orifice 57 of 45 psia for North Slope crude and 59 psia for Nigerian Light crude.

Pure water was also calculated to investigate the impact, if any, from refinery operations such as a desalter upset or some other abnormal situation which result in the introduction of water into the crude supply passing through a crude analyzer of this invention. From Table 1, it is clear that the flow rate is only minimally affected.

EXAMPLE 2

Another variable likely to affect critical flow rates through a crude analyzer of this invention involves changes in the supply pressure measured by supply pressure indicator 61 shown in FIG. 2.

TABLE 2

EFFECT OF SUPPLY PRESSURE FLUCTUATIONS ON CRITICAL FLOW THROUGH THE COMMERCIAL APPARATUS
Equivalent Length = 190 ft.
Inside d = 0.120 in.
of Coil 71

| Supply | | Upstream Pressure | | Upstream Pressure | |
|---|---|---|---|---|---|
| Press. psig | Temp. °F. | $P_u$ psia | Flow #/hr | $P_u$ psia | Flow #/hr |
| NORTH SLOPE CRUDE | | | | | |
| 450 | 353 | 52 | 331 | 47.5 | 329 |
| 400 | 353 | 49 | 308 | 45 | 305 |
| 350 | 353 | 46 | 283 | 42 | 281 |
| NIGERIAN LIGHT CRUDE | | | | | |
| 450 | 353 | 74.5 | 354 | 63 | 336 |
| 400 | 353 | 70 | 328 | 49 | 310 |
| 350 | 353 | 65.5 | 299 | 55 | 283 |

From Table 2, it is clear that the pressure upstream, $P_u$, for a supply pressure varying from 450 to 350 psig is only about 10%. A change in flow rate in pounds per hour of less than about 50 lbs per hour is the result of these variations in supply pressure.

EXAMPLE 3

Still another variable likely to affect critical flow rates through a crude analyzer of this invention involves changes in the supply temperature measured by supply temperature indicator 60 shown in FIG. 2. Using a steam jacketed coil in contact with 125 lbs steam having a temperature at 353° F. was observed to cause such rapid temperature equilibration that regardless of supply temperature, the temperature measured just upstream of the free expansion by temperature indicator 54 was 353° F.

EXAMPLE 4

Although EXAMPLES 1-3 are critical to establishing the utility of this invention as not requiring any moving parts, the critical operating feature of this invention is an observed change in temperature, $D_T$, or delta T. Delta T or $D_T$ can be determined from the difference in temperature of a crude feed across two different zones. The first, $D_T'$, is across the entire apparatus between the crude supply temperature, $T_s$, measured by supply temperature indicator 60 and the temperature, $T_d$, measured downstream of the expansion by downstream temperature indicator 56. The second, $D_T$, which is believed more reliable, can be determined from the difference in temperature just across the free expansion, i.e. the temperature just upstream of the expansion, $T_u$, measured by upstream temperature indicator 54 and the temperature, $T_d$, measured as above downstream of the expansion.

For this invention to be useful $D_T$ or $D_T'$ must be a useful measure of a crude type. Conceptually, all factors except the petroleum crude being equal, the greater the $D_T$ or $D_T'$, the lighter the crude. This is the case because in a light crude, there are more readily volatilizable components which will provide more phase change across the two-phase critical flow expansion.

The graph in FIG. 4 establishes a linear correlation between percent by volume of components volatile at about 625° F. (330° C.) and one atmosphere pressure for a series of petroleum crudes and the observed temperatures downstream of an isenthalpic flash, flash temperature, respectively corresponding to each petroleum crudes provided the upstream temperatures are constant. Here two different upstream or preflash temperatures of 400° F. (204° C.) and 260° F. (127° C.) were used. For both preflash temperatures, the upstream pressure before the isenthalpic flash was 100 psig and the downstream pressure after the flash was 75 mm of Hg absolute.

FIG. 4 based upon the results of isenthalpic flashes of a variety of crudes demonstreates that $D_T$ or $D_T'$ which corresponds to a difference between preflash temperature (here 400° F. and 260° F.) and observed temperatures downstream of the flash, flash temperatures, can be used to determine crude type in the sense of percent by volume of volatiles off at 625° F. true boiling point (TBP) cut point.

EXAMPLE 5

Although EXAMPLES 1–4 are critical to establishing the operability of this invention, they are not sufficient without taking into account the impact of actual refinery operations which involve supply pressure fluctuations, vacuum column pressure fluctuations, crude supply changes and various combinations thereof on observed $D_T$. The impact of actual refinery operations on the observed $D_T$ as shown in this EXAMPLE 5 are sufficiently small provided a difference in $D_T$ of at least 5° F. is established.

The observed change in temperature $D_T$, measured at temperature indicators 54 and 56 will depend upon changes in downstream pressure, $P_d$, which is the pressure after the expansion in zone 47 shown in FIG. 3. This is clear because the amount of vaporization on expansion depends upon the pressure downstream of the expansion.

The effect of vacuum column or vacuum still 20, pressure fluctuations on the change in temperature calculated at temperature indicators 54 and 56 is summarized in Table 3 below.

TABLE 3

EFFECT OF VACUUM COLUMN PRESSURE FLUCTUATIONS ON T USING THE COMMERCIAL APPARATUS
Equivalent Length = 190 ft.
Inside d = 0.120 in.
of Coil 71

| Supply | | Vacuum Column | Insulated | Steam-Jacketed |
|---|---|---|---|---|
| Press. psig | Temp. °F. | Pressure mm Hg | $T_u$-$T_D$ °F. | $T_u$-$T_D$ °F. |
| NORTH SLOPE CRUDE | | | | |
| 400 | 353 | 75 | 46 | 48 |
| 400 | 353 | 95 | 44 | 46 |
| NIGERIAN LIGHT CRUDE | | | | |
| 400 | 353 | 75 | 78 | 81 |
| 400 | 353 | 95 | 75 | 77 |

It is anticipated that a large change in vacuum still pressure for a commercial unit is on the order of plus or minus 20 millimeters (mm) of mercury (Hg). For North Slope Crude, a 20 mm Hg increase in vacuum column pressure decreased the observed temperature change by 2° F. For Nigerian Light Crude, the change in temperature is 3° F. These results indicating that vacuum column pressure fluctuations can be ignored.

Sensitivity to various combinations of supply pressure and temperature and vacuum column pressure variations were examined and found to be unimportant. These results are summarized in the following Table 4.

TABLE 4

| Case | A | B | C | D | E | F | G | H | I | J | K | L |
|---|---|---|---|---|---|---|---|---|---|---|---|---|
| Crude Supply | Nil | Nil | Nil | Nil | Nil | Nil | Nil | Nil | Nil | Nil | Nil | Nil |
| Pressure(psig) | 400 | 450 | 350 | 400 | 400 | 450 | 340 | 450 | 350 | 400 | 450 | 350 |
| Temperature(°F.) | 353 | 353 | 353 | 400 | 300 | 400 | 300 | 300 | 400 | 353 | 353 | 353 |
| Vacuum Column Pressure(mm Hg) | 75 | 75 | 75 | 75 | 75 | 75 | 75 | 75 | 75 | 75 | 75 | 75 |
| Insulated | Yes | Yes | Yes | Yes | Yes | Yes | Yes | Yes | Yes | No | No | No |
| Steam-Jacketed | No | No | No | No | No | No | No | No | No | Yes | Yes | Yes |
| Flow (#/hr) | 310 | 336 | 283 | 290 | — | 316 | 295 | — | 261 | 328 | 354 | 299 |
| Pi(psia) | 59 | 63 | 55 | 63.5 | — | 68 | 48 | — | 58 | 70 | 74.5 | 65.5 |
| $T_s$-$T_D$(°F.) | 86 | 86 | 86 | 96 | 72 | 96 | 72 | 72 | 96 | 81 | 83 | 80 |
| $T_u$-$T_D$(°F.) | 78 | 80 | 77 | 80 | — | 82 | 72 | — | 78 | 81 | 83 | 80 |
| Case | M | N | O | P | Q | R | S | T | U | V | W | X |
| Crude Supply | Nil | Nil | Nil | Nil | Nil | Nil | Nil | Nil | Nil | Nil | Nil | Nil |
| Pressure(psig) | 400 | 450 | 350 | 400 | 400 | 450 | 340 | 450 | 350 | 400 | 450 | 350 |
| Temperature(°F.) | 353 | 353 | 353 | 400 | 300 | 400 | 300 | 300 | 400 | 353 | 353 | 353 |
| Vacuum Column Pressure(mm Hg) | 95 | 95 | 95 | 95 | 95 | 95 | 95 | 95 | 95 | 95 | 95 | 95 |
| Insulated | Yes | Yes | Yes | Yes | Yes | Yes | Yes | Yes | Yes | No | No | No |
| Steam-Jacketed | No | No | No | No | No | No | No | No | No | Yes | Yes | Yes |
| Flow(#/hr) | 310 | 336 | 283 | 290 | — | 316 | 295 | — | 261 | 328 | 354 | 299 |
| Pi(psia) | 59 | 63 | 55 | 63.5 | — | 68 | 48 | — | 58 | 70 | 74.5 | 65.5 |
| $T_s$-$T_D$(°F.) | 83 | 83 | 83 | 93 | 69 | 93 | 69 | 69 | 93 | 77 | 80 | 77 |
| $T_u$-$T_D$(°F.) | 75 | 77 | 74 | 77 | — | 79 | 69 | — | 75 | 77 | 80 | 77 |

Nil = Nigerian Light

The results of EXAMPLE 5 indicate that anticipated supply pressure and temperature fluctuations have a minimal affect on critical flow except when supply temperature drops significantly. Steam jacketing the coil eliminated any this problem from a low supply temperature. For both North Slope and Nigerian Light Crudes, the only case where the observed temperature change varied greater than 5° F. from the base condition case was for the case of low supply temperature and pressure and high vacuum column pressure using an insulated coil. Steam jacketing the coil reduces the temperature change variation to only 1° F.

In summary, the design given in FIG. 3 for the pressure reducing coil is adequate to give the desired critical flow rate across an expansion to a 1½" inside diameter pipe. The sensitivity study shows that anticipated fluctuations to supply temperature and pressure do not dramatically affect (1) the observed temperature change, i.e., $D_T$, at temperature indicators 54 and 56, respectively, or (2) the critical flow through the pressure reducing coil, if the coil is steam jacketed.

Specific examples of this invention discussed in this specification are intended to be illustrative only. Variations on such examples are clear to one of skill in the art based upon the teachings in this specification and are intended to be part of this invention.

The invention which is claimed is:

1. An analyzer for determining volatile composition changes of a distillable material comprising:
    (a) a first means for causing at least a portion of said material to be at a temperature and at a pressure so that a difference in temperature of said portion of said material across an isenthalpic expansion at critical flow conditions would be at least about 5° F.;
    (b) a second means for carrying out said isenthalpic expansion on said at least a portion of said material;
    (c) a third means for measuring at least two temperatures of said material where said at least two temperatures are a first and a second temperature, said first temperature being measured upstream of said expansion and said second temperature being measured downstream from said expansion; and
    (d) a fourth means for maintaining pressure downstream of said expansion to a value which does not vary by an amount in excess of about 20% of said pressure downstream of said expansion.

2. The analyzer of claim 1 wherein said value does not vary by an amount in excess of about 10% of said pressure downstream from said expansion.

3. The analyzer of claim 1, wherein said distillable material is a hydrocarbon feedstock.

4. The analyzer of claim 3, wherein upstream of said expansion, said temperature is in the range of about 200° F. to about 650° F. and said pressure in pounds per square inch absolute is in the range of about 5 to about 165.

5. The analyzer of claims 1, 2, 3, or 4, wherein there are no moving parts.

6. In equipment useful for processing a distillable material into various boiling fractions thereof, the improvement comprising in combination therewith an on-line analyzer for determining changes in volatile composition of said material prior to processing said material into various boiling fractions comprising:
    (a) a first means for causing at least a portion of said material to be at a temperature and at a pressure so that a difference in temperature of said portion of said material across an isenthalpic expansion thereof at critical flow conditions would be at least about 5° F.;
    (b) a second means for carrying out said isenthalpic expansion on said at least a portion of said material;
    (c) a third means for measuring at least two temperatures of said material where said at least two temperatures are a first and a second temperature, said first temperature being measured upstream of said expansion, and said second temperature being measured downstream from said expansion; and
    (d) a fourth means for maintaining pressure downstream from said expansion to a value which does not vary by an amount in excess of about 20% of said pressure downstream from said expansion.

7. The analyzer of claim 6, wherein said value does not vary by an amount in excess of about 10% of said pressure downstream from said expansion.

8. In the improved equipment of claims 6 or 7, wherein said distillable material is a hydrocarbon feedstock and said first means causes both said temperature to be in the range of about 200° F. to about 650° F., and said pressure in psia to be in the range of about 5 to about 165.

9. A process for determining a volatile composition of a distillable material while said material is being transferred to a distillation column, said process comprising: diverting at least a portion of said material to form a first stream; causing at least a portion of said first stream to be at a temperature and a pressure to form a second stream wherein a difference in temperature of said second stream across an isenthalpic expansion at critical flow conditions, to be carried out later in said process, would be at least about 5° F.; expanding said second stream at said isenthalpic and critical flow conditions while maintaining pressure downstream of said expansion to a value that does not vary by an amount in excess of about 20% thereof; whereby said temperature change across said expansion in said second stream is a measure of volatile composition of said second stream.

10. The process of claim 9, wherein said value does not vary by an amount in excess of about 10% thereof.

11. The process of claims 9 or 10, wherein said distillable material is a hydrocarbon feedstock and said temperature of said second stream is in the range of about 200° F. to about 650° F. and said pressure of said second stream in psia is in the range of about 5 to about 165.

12. A process for determining a volatile composition of a distillable material while said material is being transferred to a distillation column, said process comprising: diverting at least a portion of said material to form a first stream; causing at least a portion of said first stream to be at a temperature and a pressure to form a second stream wherein a difference in temperature of said second stream across an isenthalpic expansion and critical flow conditions, to be carried out later in said process, would be at least about 5° F.; expanding said second stream at said isenthalpic and critical flow conditions to form a third stream downstream of said expansion; and transferring said third stream to a vacuum still having a design capacity to maintain pressure within said vacuum still to a value that does not vary by an amount in excess of about 20% of that value.

13. The process of claim 12, wherein the flow rate of said third stream determined by critical flow conditions is at a rate that does not vary by a value in excess of 10% of an average operating value of said flow rate.

14. The process of claim 13, wherein said flow rate in pounds per hour is in the range of about 20 to about 600.

15. The process of claim 13, wherein said flow rate in pounds per hour is in the range of about 20 to about 500.

16. The process of claim 12, wherein said design capacity in pressure in millimetrs of mercury is in the range of about 30 to about 250.

17. The process of claim 12, wherein said temperature and said pressure of said second stream is in the range of about 200° F. to about 650° F. and about 5 psia to about 165 psia, respectively.

* * * * *